(12) United States Patent
Matsuki et al.

(10) Patent No.: US 11,823,386 B2
(45) Date of Patent: *Nov. 21, 2023

(54) DIAGNOSIS ASSISTANCE APPARATUS, AND INFORMATION PROCESSING METHOD

(71) Applicant: CANON KABUSHIKI KAISHA, Tokyo (JP)

(72) Inventors: Naoki Matsuki, Tokyo (JP); Masami Kawagishi, Kawasaki (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/862,715

(22) Filed: Jul. 12, 2022

(65) Prior Publication Data

US 2022/0358651 A1 Nov. 10, 2022

Related U.S. Application Data

(63) Continuation of application No. 16/845,774, filed on Apr. 10, 2020, now Pat. No. 11,423,537, which is a (Continued)

(30) Foreign Application Priority Data

Oct. 13, 2017 (JP) ................. 2017-199600

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/5217* (2013.01); *G06F 18/214* (2023.01); *G06F 18/217* (2023.01); *G06F 18/24* (2023.01); *G06V 10/82* (2022.01); *G06T 2207/10081* (2013.01);
(Continued)

(58) Field of Classification Search
CPC ......... G06T 7/0012; G06T 2207/10081; G06T 2207/10088; G06T 2207/20081; G06F 18/217; G06F 18/24; G06F 18/214; A61B 6/032; A61B 6/5217; G06V 2201/03; G06V 10/82
See application file for complete search history.

(56) References Cited

U.S. PATENT DOCUMENTS 7,894,676 B2 2/2011 Iizuka et al.
8,798,345 B2 8/2014 Sasaki et al.
(Continued)

FOREIGN PATENT DOCUMENTS

CN 101742961 A 6/2010
CN 101808572 A 8/2010
(Continued)

*Primary Examiner* — Utpal D Shah
(74) *Attorney, Agent, or Firm* — VENABLE LLP

(57) ABSTRACT

Diagnosis is inferred by using at least one of a plurality of inferencers configured to infer diagnosis from a medical image and by using a medical image as an input into the at least one of the plurality of inferencers, and the inferred diagnosis is represented.

12 Claims, 10 Drawing Sheets

Related U.S. Application Data continuation of application No. PCT/JP2018/037502, filed on Oct. 9, 2018.

(51) Int. Cl.
*A61B 6/00* (2006.01)
*G06F 18/24* (2023.01)
*G06F 18/214* (2023.01)
*G06F 18/21* (2023.01)
*G06V 10/82* (2022.01)

(52) U.S. Cl.
CPC ............... *G06T 2207/10088* (2013.01); *G06T 2207/20081* (2013.01); *G06V 2201/03* (2022.01)

(56) References Cited

U.S. PATENT DOCUMENTS

| | | | |
|---|---|---|---|
| 8,880,455 B2 | 11/2014 | Kawagishi et al. | |
| 9,361,580 B2 | 6/2016 | Kawagishi | |
| 9,384,326 B2 | 7/2016 | Kawagishi et al. | |
| 9,436,915 B2 | 9/2016 | Kawagishi et al. | |
| 9,519,866 B2* | 12/2016 | Kawagishi | G06F 16/26 |
| 9,715,657 B2* | 7/2017 | Kawagishi | G16Z 99/00 |
| 9,734,300 B2* | 8/2017 | Kawagishi | A61B 6/461 |
| 9,779,354 B2 | 10/2017 | Hagawa et al. | |
| 9,852,269 B2 | 12/2017 | Sakagawa et al. | |
| 9,916,425 B2* | 3/2018 | Kawagishi | G16H 50/20 |
| 9,940,438 B2* | 4/2018 | Kawagishi | G16H 50/70 |
| 10,049,445 B2* | 8/2018 | Nakano | G06T 7/0012 |
| 10,068,056 B2 | 9/2018 | Miyasa et al. | |
| 10,169,863 B2* | 1/2019 | Reicher | G06N 20/00 |
| 10,282,671 B2 | 5/2019 | Kawagishi | |
| 10,297,352 B2 | 5/2019 | Sakagawa et al. | |
| 10,861,606 B2* | 12/2020 | Kawagishi | G16H 50/70 |
| 11,087,463 B2* | 8/2021 | Peng | G06N 20/00 |
| 2007/0237377 A1* | 10/2007 | Oosawa | G16H 50/20 382/128 |
| 2010/0189366 A1 | 7/2010 | Iizuka et al. | |
| 2010/0250275 A1 | 9/2010 | Sakagawa et al. | |
| 2010/0256459 A1 | 10/2010 | Miyasa et al. | |
| 2010/0332441 A1 | 12/2010 | Kawagishi et al. | |
| 2011/0166879 A1 | 7/2011 | Lee et al. | |
| 2011/0199390 A1 | 8/2011 | Iizuka et al. | |
| 2011/0213748 A1 | 9/2011 | Kawagishi et al. | |
| 2011/0274338 A1* | 11/2011 | Park | A61B 5/4331 382/133 |
| 2012/0054652 A1 | 3/2012 | Kawagishi et al. | |
| 2012/0183187 A1 | 7/2012 | Sasaki et al. | |
| 2012/0254101 A1 | 10/2012 | Kawagishi | |
| 2014/0195472 A1* | 7/2014 | Kawagishi | G16Z 99/00 706/46 |
| 2015/0006447 A1* | 1/2015 | Kawagishi | G06N 5/04 706/12 |
| 2015/0012474 A1 | 1/2015 | Kawagishi et al. | |
| 2015/0019473 A1* | 1/2015 | Yakami | G16H 50/20 706/52 |
| 2015/0072371 A1* | 3/2015 | Marugame | G16Z 99/00 702/19 |
| 2016/0260014 A1 | 9/2016 | Hagawa et al. | |
| 2016/0357925 A1 | 12/2016 | Kawagishi et al. | |
| 2018/0025112 A1* | 1/2018 | Takeda | G06V 10/764 705/2 |
| 2018/0137942 A1 | 5/2018 | Sakagawa et al. | |
| 2018/0204644 A1 | 7/2018 | Kawagishi | |
| 2019/0027252 A1* | 1/2019 | Calhoun | A61B 6/502 |
| 2019/0042959 A1 | 2/2019 | Kawagishi | |
| 2020/0085290 A1* | 3/2020 | Wang | G06N 20/20 |

FOREIGN PATENT DOCUMENTS

| | | |
|---|---|---|
| CN | 101808574 A | 8/2010 |
| CN | 102473206 A | 5/2012 |
| CN | 102722633 A | 10/2012 |
| JP | 2000-155680 A | 6/2000 |
| JP | 2006-43007 A | 2/2006 |
| JP | 2010-200840 A | 9/2010 |
| JP | 2010-252989 A | 11/2010 |
| JP | 2012-503812 A | 2/2012 |
| JP | 2012-69089 A | 4/2012 |
| JP | 2012-235796 A | 12/2012 |
| JP | 2012-249964 A | 12/2012 |
| JP | 2014-29644 A | 2/2014 |
| JP | 2014-147659 A | 8/2014 |
| JP | 2017-84320 A | 5/2017 |
| JP | 2017-153691 A | 9/2017 |
| WO | 2010/035161 A1 | 4/2010 |
| WO | 2013/001584 A1 | 1/2013 |

\* cited by examiner

FIG. 4

| n | $F_n$ | nk | $f_{nk}$ |
|---|---|---|---|
| 1 | SHAPE | 11 | SPHERICAL |
| | | 12 | LOBULAR |
| | | 13 | POLYGONAL |
| | | 14 | IRREGULAR |
| 2 | CUT | 21 | INTENSE |
| | | 22 | MILD |
| | | 23 | NONE |
| 3 | SERRATED EDGE | 31 | INTENSE |
| | | 32 | MILD |
| | | 33 | NONE |
| ... | | | |
| N | INVOLVEMENT (BRONCHUS) | N1 | PRESENCE |
| | | N2 | DOUBT |
| | | N3 | ABSENCE |

| j | $C_j$ | jk | $c_{jk}$ |
|---|---|---|---|
| 1 | FEVER | 11 | PRESENCE |
| | | 12 | ABSENCE |
| 2 | COUGH | 21 | PRESENCE |
| | | 22 | ABSENCE |
| 3 | BLOODY SPUTUM | 31 | PRESENCE |
| | | 32 | ABSENCE |
| ... | | | |
| J | CEA | \<CONTINUOUS VALUE $c_J$\> | |

FIG. 5

| $e_v$ | $I(e_v)$ |
|---|---|
| $i_1$ | 0.21 |
| $i_2$ | -0.16 |
| $i_3$ | 0.15 |
| ... | |
| $i_M$ | 0.02 |
| $c_{11}$ | -0.13 |
| ... | |
| $c_J$ | 0.19 |

DIAGNOSIS ASSISTANCE APPARATUS, AND INFORMATION PROCESSING METHOD

CROSS-REFERENCE TO RELATED APPLICATIONS

This application is a continuation of U.S. patent application Ser. No. 16/845,774 filed on Apr. 10, 2020, which is a Continuation of International Patent Application No. PCT/JP2018/037502, filed Oct. 9, 2018, which claims the benefit of Japanese Patent Application No. 2017-199600, filed Oct. 13, 2017, all of which are hereby incorporated by reference herein in their entirety.

BACKGROUND OF THE INVENTION

Field of the Invention

The present disclosure relates to a diagnosis assistance apparatus, an information processing method, a diagnosis assistance system, and a computer readable medium.

Description of the Related Art

In recent years, various kinds of medical information have been used for diagnosis, and expectations have been raised for a technique related to a system for using a result that is acquired by analyzing medical information such as a medical image by a computer to support diagnosis. Japanese Patent Application Laid-Open No. 2014-29644 discloses a system that searches a similar case based on an image feature amount that is acquired by analyzing a medical image and an interpretation item of a past case and that provides a user with information that what search result is acquired by using the interpretation item for the search.

In some cases where a doctor uses a result that is acquired by analyzing medical information by a computer to support diagnosis, the doctor cannot decide whether the result is useful if the doctor is provided with only the result of analysis. According to a technique disclosed in Japanese Patent Application Laid-Open No. 2014-29644, only a past case that is closely related to the interpretation item used for the search is represented, and there is a possibility that whether information is useful for target diagnosis cannot be grasped.

SUMMARY OF THE INVENTION

A diagnosis assistance apparatus according to an embodiment of the present invention includes a plurality of inferencers configured to infer diagnosis from a medical image, an inference means configured to infer diagnosis by using at least one of the plurality of inferencers and by using a medical image as an input into the at least one of the plurality of inferencers, and a representation means configured to represent the diagnosis that is inferred by the inference means.

Further features of the present invention will become apparent from the following description of exemplary embodiments with reference to the attached drawings.

BRIEF DESCRIPTION OF THE DRAWINGS

FIG. 4 illustrates an example of information that is acquired by the diagnosis assistance apparatus according to the embodiment of the present invention.

FIG. 5 illustrates an example of information that is acquired by the diagnosis assistance apparatus according to the embodiment of the present invention.

DESCRIPTION OF THE EMBODIMENTS

Figure 1:
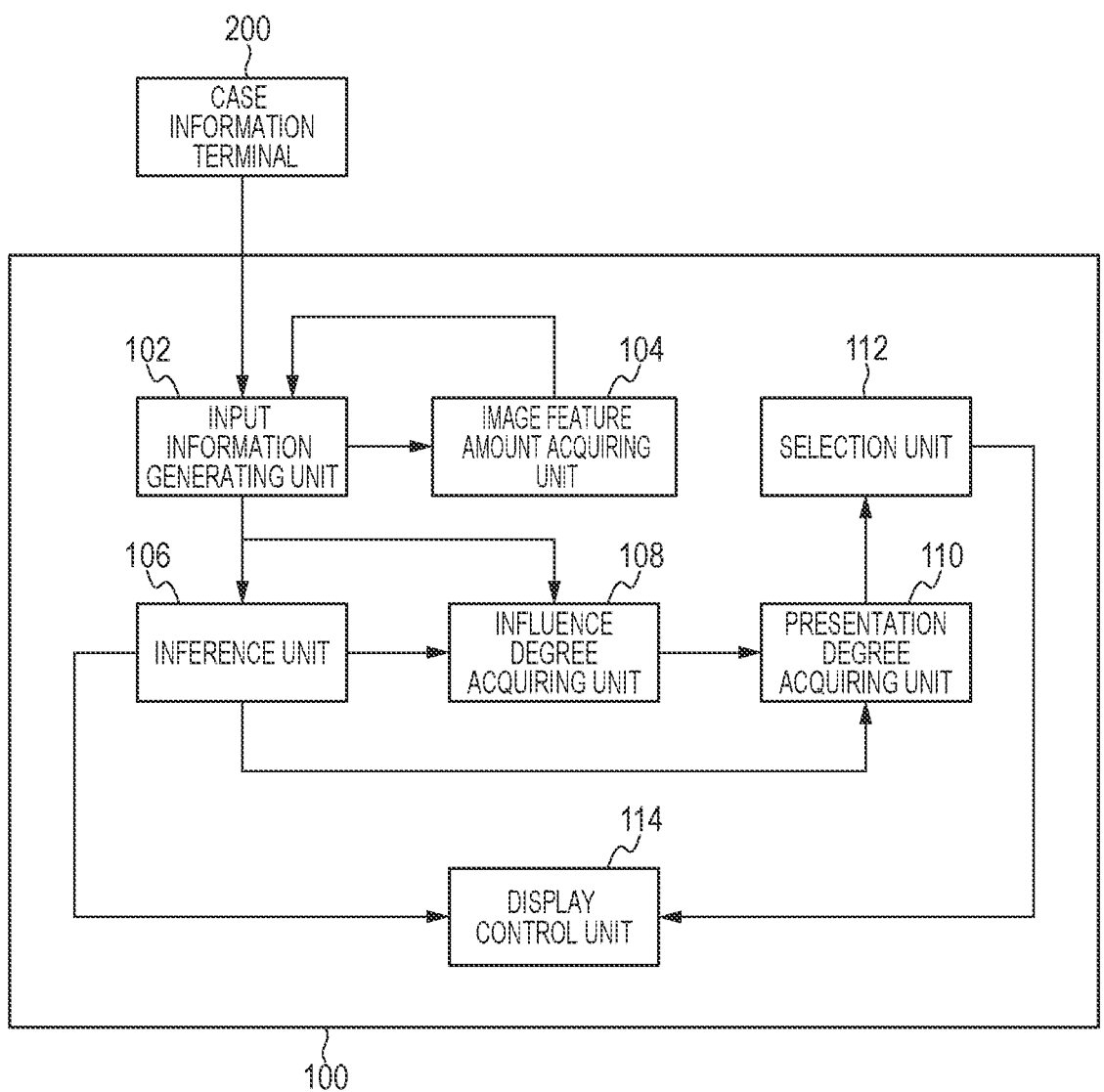
FIG. 1 illustrates an example of the functional components of a diagnosis assistance apparatus according to an embodiment of the present invention.

Embodiments of the present invention will hereinafter be described with reference to the drawings.

First Embodiment

In the medical industry, image diagnosis is made for diagnosis based on a medical image that is acquired by an imaging apparatus such as an X-ray CT (Computer Tomography) apparatus or an MRI (Magnetic Resonance Imaging) apparatus. Interpretation described herein means that a medical image is observed to derive diagnosis. In the image diagnosis, a radiologist who specializes in the image diagnosis carries out interpretation, for example, in response to a request for the interpretation from a physician. The radiologist makes a comprehensive decision from various measurement values or findings (referred to below as image findings) that are acquired from an image to identify a lesion that is drawn in a medical image or a symptom of a patient to be diagnosed. The radiologist records details from which diagnosis is derived in an interpretation report for the requesting physician by using the image findings or the measurement values.

To assist the interpretation, a proposed system represents a result that is acquired by analyzing medical information by a computer. When a doctor uses the result of analysis, information about an evidence for the result is preferably represented. However, in some cases where information (referred to below as input information) that is input for the analysis is information such as an image feature amount that is a numerical value expressing a feature that is drawn in an image, the information is difficult for a user to understand even if information that affected the result is identified and represented. It is an object of a diagnosis assistance apparatus according to a first embodiment of the present invention to represent information (referred to below as reference information) that can be a clue to derivation of an inference result and that the user can intuitively understand even if the input information includes the information such as the image feature amount that is difficult for the user to understand. An example of the reference information that the user can intuitively understand is information about findings that express a feature of a lesion region by a language.

Details will now be described. A diagnosis assistance apparatus 100 according to the first embodiment acquires, for example, a medical image to be the subject of the interpretation and information written in, for example, an electronic medical record and represents information (reference information) that can be a clue to diagnosis for diagnosis assistance.

In the following description, the diagnosis assistance apparatus 100 acquires a medical image related to the interpretation of abnormal shadow on the lungs, information with which the medical image is supplemented, and information (referred to below as clinical information) about, for example, blood test values such as tumor markers and a past medical history. In an example described below, the input information is generated based on the acquired information. From the input information, the information (reference information) that can be the clue to the diagnosis is generated in a form that the user (doctor) can understand, and the information is represented. A subject is naturally not limited thereto. The diagnosis, the image feature amount, the image findings, and the clinical information, for example, are described below by way of example for a description of processes in the processing of the diagnosis assistance apparatus.

FIG. 1 illustrates an example of the functional components of the diagnosis assistance apparatus 100. The diagnosis assistance apparatus 100 is communicably connected to a case information terminal 200. The diagnosis assistance apparatus 100 includes an input information generating unit 102, an image feature amount acquiring unit 104, an inference unit 106, an influence degree acquiring unit 108, a presentation degree acquiring unit 110, a selection unit 112, and a display control unit 114. The functional components of the diagnosis assistance apparatus 100 are connected by using, for example, an internal bus.

The case information terminal 200 acquires information about a case to be diagnosed from a server (not illustrated). An example of the information about the case is medical information such as a medical image or clinical information that is written in an electronic medical record. The case information terminal 200 may be connected to an external storage device (not illustrated) such as a FDD, a HDD, a CD drive, a DVD drive, a MO drive, or a ZIP drive and may acquire the medical information from the external storage device.

The case information terminal 200 may use the display control unit 114 to cause a monitor 205 to display the medical information in a form that enables the user to carry out the interpretation. That is, the case information terminal 200 uses the display control unit 114 to provide a GUI through which the user inputs coordinate information about a region on a medical image that is displayed on the monitor 205, and the user thinks the region contains the abnormal shadow. Alternately, the case information terminal 200 may use the display control unit 114 to provide a GUI though which the user inputs the image findings regarding the region on the medical image that is displayed on the monitor 205. The case information terminal 200 acquires the information that is inputted by user though the GUI as information (referred to below as supplementary information) with which the medical image is supplemented.

The case information terminal 200 transmits the medical information such as the medical image and the clinical information and the supplementary information to the diagnosis assistance apparatus 100 via, for example, a network.

The input information generating unit 102 generates the input information based on the information that is transmitted from the case information terminal 200 to the diagnosis assistance apparatus 100, such as the medical image, the clinical information, and the supplementary information. The input information described herein means a set, elements of which are pieces of information used as an input for inference by the inference unit 106. According to the first embodiment, the input information generating unit 102 outputs the medical image and the supplementary information to the image feature amount acquiring unit 104 and acquires the image feature amount that is outputted from the image feature amount acquiring unit 104 in response to the output. The input information generating unit 102 determines the acquired image feature amount and the clinical information to be the input information and outputs the input information to the inference unit 106 and the influence degree acquiring unit 108.

The image feature amount acquiring unit 104 acquires the image feature amount based on the medical image and the supplementary information that are outputted from the input information generating unit 102. The image feature amount acquiring unit 104 performs image processing on the medical image to be the subject of the interpretation and acquires the image feature amount of the medical image. For example, in the case where the input information generating unit 102 outputs supplementary information such as coordinate information about an abnormal region, the image feature amount acquiring unit 104 can acquire the image feature amount of the abnormal region that is expressed by the coordinate information. The image feature amount acquiring unit 104 outputs the acquired image feature amount to the input information generating unit 102.

The inference unit 106 infers the diagnosis of a target case by using the input information that is generated by the input information generating unit 102 as an input. In an example described according to the first embodiment, the diagnosis that is inferred relates to the abnormal shadow on the lungs. The inference unit 106 may acquire the position of the abnormal shadow based on the supplementary information that is outputted from the input information generating unit 102 or may identify the position by image processing. The inference unit 106 acquires, as the inference result, probability that the abnormal shadow on the medical image corresponds to specific diagnosis. The acquired inference result is outputted to the influence degree acquiring unit 108 and the display control unit 114. The inference unit 106 is an example of an inference means.

The influence degree acquiring unit 108 acquires the influence degree of each of elements that are included in the input information on the inference result by using the input information that is generated by the input information generating unit 102 and the inference result that is outputted from the inference unit 106. The influence degree acquiring unit 108 outputs the acquired influence degree of each element to the presentation degree acquiring unit 110. The influence degree acquiring unit 108 is an example of an influence degree acquiring means.

The presentation degree acquiring unit 110 acquires the presentation degree of information that is a candidate of the reference information by using the influence degree that is acquired by the influence degree acquiring unit 108. The reference information is represented to the user by the display control unit 114 as an evidence for inference by the inference unit 106. The presentation degree is an indicator that expresses a degree at which, among candidates of the reference information, the candidate is preferably represented as the reference information. The presentation degree acquiring unit 110 acquires the image findings based on the image feature amount. The image feature amount, the clinical information, and the image findings in the input information correspond to candidates of the reference information. The presentation degree acquiring unit 110 outputs the acquired presentation degree of each candidate of the reference information to the selection unit 112. The presentation degree acquiring unit 110 is an example of a findings acquiring means.

The selection unit 112 selects the reference information, that is, information to be represented as the evidence for inference based on the influence degree of each candidate of the reference information that is acquired by the presentation degree acquiring unit 110. The selection unit 112 outputs the selected information to the display control unit 114. The selection unit 112 is an example of a selection means.

The display control unit 114 represents the inference result that is outputted by the inference unit 106 and the reference information that is selected by the selection unit 112 to the user. The display control unit 114 controls a content that is displayed on the monitor 205 based on the inference result and the reference information.

At least a part of the structure of the diagnosis assistance apparatus 100 illustrated in FIG. 1 may be a separated apparatus. The function thereof may be performed by software. According to the first embodiment, software may function as components.

Figure 2:
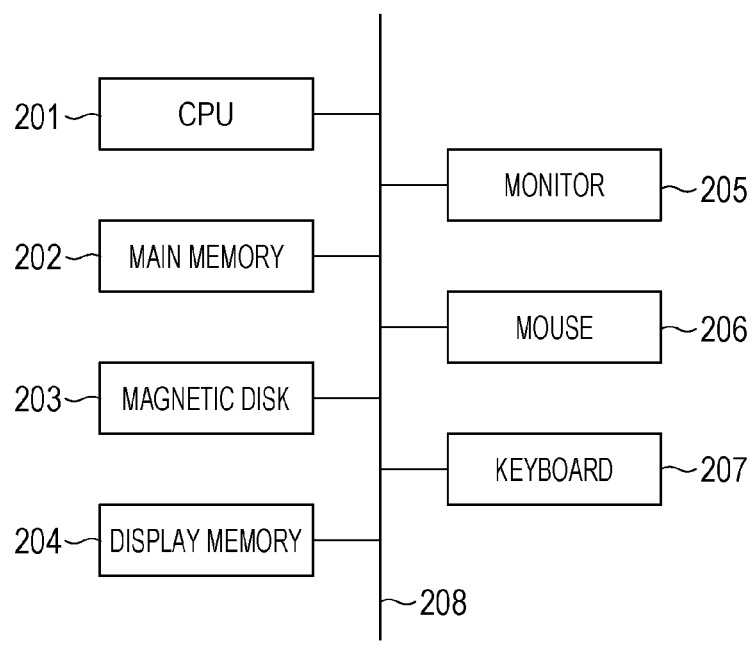
FIG. 2 illustrates an example of the hardware configuration of the diagnosis assistance apparatus according to the embodiment of the present invention.

FIG. 2 illustrates an example of the hardware configuration of the diagnosis assistance apparatus 100. A CPU 201 mainly controls operation of each component. A main memory 202 stores a control program that the CPU 201 runs and provides a work area used when the CPU 201 runs the program. A magnetic disk 203 stores an operating system (OS), a device driver of a peripheral device, and programs for running various kinds of application software including a program for performing a process described later. The function (software) of the diagnosis assistance apparatus 100 illustrated in FIG. 1 and processes in flowcharts described later are performed by running the programs that are stored in the main memory 202 and the magnetic disk 203 by the CPU 201.

A display memory 204 temporarily stores display data for display on the monitor 205. The monitor 205 is, for example, a CRT monitor or a liquid crystal monitor and displays, for example, an image or a text based on data from the display memory 204. A mouse 206 and a keyboard 207 are used for pointing input and input of, for example, a character by the user.

The above components are communicably connected to each other by using a common bus 208. The CPU 201 is an example of a processor. The diagnosis assistance apparatus 100 may include multiple processors. For example, the diagnosis assistance apparatus 100 may include a GPU for exclusive use of the processing of the inference unit 106 or may include a FPGA (Field-Programmable Gate Array) in which the function of the inference unit 106 is programmed. The main memory 202, the magnetic disk 203, and the display memory 204 are examples of a memory.

Figure 3:
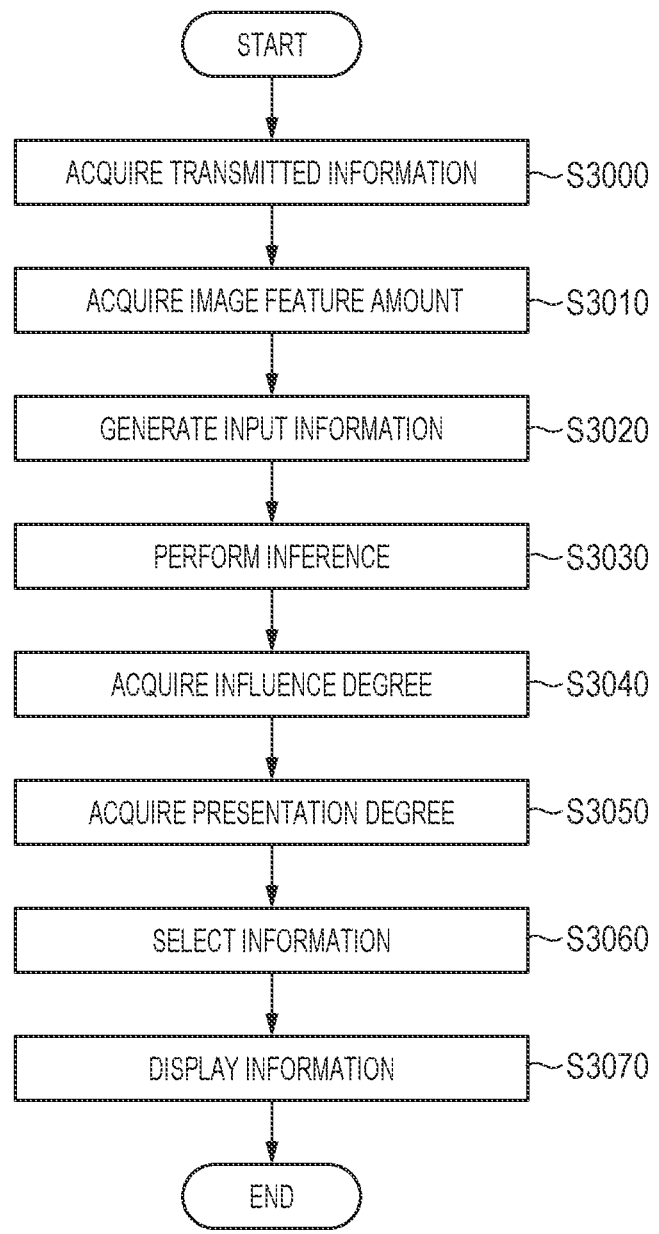
FIG. 3 is a flowchart illustrating an example of processing that is performed by the diagnosis assistance apparatus according to the embodiment of the present invention.

FIG. 3 is a flowchart illustrating an example of processing that is performed by the diagnosis assistance apparatus 100. According to the first embodiment, the processing illustrated in FIG. 3 is performed by running a program that is stored in the main memory 202 for performing the function of each component by the CPU 201.

In the following description, the image feature amount is expressed as $I_m$ (m=1 to M), the image findings are expressed as $F_n$ (n=1 to N), and the clinical information is expressed as $C_j$ (j=1 to J). Each element of $I_m$ has a continuous value. Each element of $F_n$ has a discrete value (category value). Each element of $C_j$ has a continuous value or a discrete value. In the case of the discrete values, the discrete values are expressed as $f_{nk}$ and $c_{jk}$. k has various values depending on $F_n$ and $C_j$. In the case where the image feature amount $I_m$ and the clinical information $C_j$ have continuous values, the values are expressed as $i_m$ and $c_j$.

According to the first embodiment, the image findings and the clinical information include items and values illustrated in FIG. 4 by way of example. For example, in the case of the image findings, for a "shape" in an item $F_1$, an element has any one of four values of $f_{11}$ "spherical", $f_{12}$ "lobular", $f_{13}$ "polygonal", and $f_{14}$ "irregular". For a "cut" in an item $F_2$, an element has any one of three values of $f_{21}$ "intense", $f_{22}$ "mild", and $f_{23}$ "none". For "fever" in an item $C_1$ which is included in the clinical information, an element has any one of two values of $c_{11}$ "presence" and $c_{12}$ "absence". For "CEA" (a kind of tumor marker) in an item $C_J$, an element has a continuous value $c_J$.

In the following description, a set including values of $I_m$, $F_n$, and $C_j$ as elements is expressed as E, and the input information is expressed as $E_f$. In the following description, the diagnosis is expressed as D. According to the first embodiment, the inference unit 106 infers the diagnosis related to the abnormal shadow on the lungs, and the diagnosis is inferred such that the diagnosis has any one of three values of primary lung cancer, cancer metastasis to the lungs, and another value. In the following description, the primary lung cancer, the cancer metastasis to the lungs, and the other value are expressed as $d_1$, $d_2$, and $d_3$, respectively. Inference probability of diagnosis $d_u$ (u=1, 2, 3) when the input information $E_f$ is inputted into the inference unit 106 is expressed as $P(d_u|E_f)$.

At step S3000, the input information generating unit 102 acquires the information (the medical image, the clinical information, and the supplementary information) that is transmitted from the case information terminal 200 to the diagnosis assistance apparatus 100. In an example described according to the first embodiment, only the coordinate information about the abnormal shadow is transmitted as the supplementary information.

At step S3010, the image feature amount acquiring unit 104 performs image processing based on the medical image and the supplementary information that are outputted at step S3000 to acquire the image feature amount. The image feature amount to be acquired herein may be a typical image feature amount such as a variance or an average of concentration (luminance) in a region of the image to be processed or an image feature amount based on a filter output.

According to the first embodiment, the image feature amount acquiring unit 104 refers the supplementary information (coordinate information of the abnormal shadow) that is acquired at step S3000, segments the region of the abnormal shadow from the medical image, and subsequently acquires the image feature amount by image processing.

At step S3020, the input information generating unit 102 generates the input information based on the clinical information that is acquired at step S3000 and the image feature amount that is acquired at step S3010. For example, the clinical information that is acquired at step S3000 is expressed as {$c_{12}$, $c_{22}$, ..., $c_J$}, and the image feature amount that is acquired at step S3010 is expressed as {$i_1$, $i_2$, ..., $i_M$}. In this case, the input information $E_f$ is expressed as $E_f$={$c_{12}$, $c_{22}$, ..., $c_J$, $i_1$, $i_2$, ..., $i_M$}.

At step S3030, the inference unit 106 infers the abnormal shadow on the lungs to be diagnosed based on the input information that is generated at step S3020. That is, the inference unit 106 infers the diagnosis that is derived from the medical image based on the image feature amount that expresses the feature of the region that is contained in the medical image. Specifically, P ($d_s|E_f$) is acquired. At this time, examples of an inference method include a method of using a Bayesian network, a support vector machine, or a neural network. According to the first embodiment, the Bayesian network is used.

At step S3040, the influence degree acquiring unit 108 acquires the influence degree of each element of the input information on the inference result by using the input information that is generated at step S3020 and the result of the inference performed at step S3030. That is, the influence degree acquiring unit 108 acquires the influence degree that means the degree of influence on the inference of the diagnosis for every information used as the input of the inference by the inference unit 106. According to the first embodiment, the influence degree is acquired for diagnosis $d_f$, the inference probability of which is highest among diagnoses. Specifically, the influence degree of an element $e_v$ ($e_v \in E_f$) is acquired by subtracting the inference probability of $d_f$ when only $e_v$ is removed from $E_f$ for inference from the inference probability of $d_f$ when the input information $E_f$ is used for inference. The influence degree of each element is expressed as I ($e_v$). The influence degree is defined as expression 1.

$$I(e_v) = P(d_f|E_f) - P(d_f|E_f - e_v) \quad \text{(expression 1)}$$

When I ($e_v$) is positive, the input information that does not include $e_v$ means that the inference probability of $d_f$ decreases. Accordingly, it is considered that $e_v$ is information that affirms $d_f$. When I ($e_v$) is negative, the input information that does not include $e_v$ means that the inference probability of $d_f$ increases. Accordingly, it is considered that $e_v$ is information that denies $d_f$.

At step S3050, the presentation degree acquiring unit 110 acquires the presentation degree of each candidate of the information to be represented as the reference information, that is, the evidence for inference by using the influence degree that is acquired at step S3040. The presentation degree of each element of the clinical information and the image findings has an absolute value of the influence degree that is acquired at step S3040. The presentation degree acquiring unit 110 acquires the presentation degree of each element of the image feature amount based on a relationship between the image feature amount and the image findings. Consequently, the image feature amount is converted into the image findings with the presentation degree.

According to the first embodiment, the presentation degree acquiring unit 110 searches a similar case based on the image feature amount and converts the image feature amount into the image findings with the presentation degree by using information about findings that are associated with the similar case. The similar case may be searched from a case database that is stored in the case information terminal 200 or may be searched from a case database that is stored in an external server (not illustrated) outside the diagnosis assistance apparatus 100. The image findings are added in advance to cases that are stored in the case information terminal 200 or the external server (not illustrated). That is, the presentation degree acquiring unit 110 acquires the image findings based on the image feature amount. More specifically, the presentation degree acquiring unit 110 acquires the information about the findings related to the image feature amount that is included in the input information into the inference unit 106.

Specifically, the presentation degree acquiring unit 110 uses the absolute value of the influence degree of the image feature amount as a weight to extract multiple cases with the degree of similarity by weighted similar case search. The presentation degree is acquired based on the degree of similarity between the image findings that are added to the extracted cases (target cases) and the image feature amount of a case (referred to below as a present case) that is the subject of diagnosis assistance by the diagnosis assistance apparatus. That is, each target case is an example of the similar case having an image feature amount similar to the image feature amount that is included in the input information into the inference unit 106.

The presentation degree acquiring unit 110 acquires the degree of similarity as follows. The degree of similarity Sim ($T_x$) between the present case and $T_x$ is expressed as expression 2, where $i_{Txm}$ is the image feature amount $I_m$ of each target case ($T_x$: x=1 to X). The image feature amount is a normalized value of [0, 1]. The degree of similarity Sim ($T_x$) expressed as the expression 2 is closer to 1 as the image feature amount of the present case is closer to the image feature amount of $T_x$.

$$Sim(T_x) = 1 - \frac{\sum_{m=1}^{M} \left(|I(i_m)|\sqrt{(i_m - i_{T_x m})^2}\right)}{\sum_{m=1}^{M} |I(i_m)|} \quad \text{(expression 2)}$$

The presentation degree acquiring unit 110 may acquire the degree of similarity in another manner. For example, the presentation degree acquiring unit 110 may not use the influence degree as the weight and may use Mahalanobis distance of S and $T_x$ as the degree of similarity. In this case, conversion is preferably carried out such that the degree of similarity is 1 when the Mahalanobis distance is 0.

The presentation degree acquiring unit 110 acquires the presentation degree (Pre ($f_{nk}$)) of the value of the image findings expressed as expression 3 based on the image findings that are added to each target case and the degree of similarity.

$$Pre(f_{nk}) = \frac{1}{X} \sum_{x=1}^{X} (Sim(T_x) \cdot \delta_x(f_{nk})) \quad \text{(expression 3)}$$

In the expression 3, $\delta_x$ ($f_{nk}$) is 1 if the value $f_{nk}$ of the image findings is added to $T_x$ and 0 if not. The expression 3 expresses that the presentation degree of the value of the image findings increases as frequency at which the value of the image findings is common in a target case group having a high degree of similarity increases. That is, the presentation degree acquiring unit 110 acquires the presentation degree based on the degree of similarity and statistics information that expresses frequency at which the image findings are associated with the target case in the target case group.

In the above example, the presentation degree acquiring unit 110 acquires the presentation degree by using all of data (X cases) included in the database that stores the similar cases but is not limited thereto. The presentation degree acquiring unit 110 may acquire the presentation degree by using only a top X' case regarding the degree of similarity, or may acquire the presentation degree in a manner in which a threshold is set and only an X" case having a degree of similarity higher than the threshold is used.

At step S3060, the selection unit 112 selects the information to be represented as the evidence for inference based on the presentation degree that is acquired at step S3050. The selection unit 112 selects the information to be represented as the evidence for inference from the image findings that are acquired at S3050 and elements except for the image feature amount in the input information into the inference unit 106. The information that is selected by the selection unit 112 corresponds to the reference information, that is, the information to be represented as the evidence for inference. That is, the selection unit 112 selects the information to be represented as the evidence for inference based on the presentation degree that is a value based on the degree of similarity between the image feature amount that is included in the input information into the inference unit 106 and the image feature amount of the similar case, and the statistics information that expresses the frequency at which the image findings are associated with the similar case.

According to the first embodiment, three pieces of information are selected in descending order of the magnitude of the presentation degree. However, in the case where a single item (for example, $F_n$) of the image findings can have multiple values (for example, $f_{n1}$ and $f_{n2}$), only the value when the presentation degree is highest is selected, and the other values are ignored. A selection number and a selection method are naturally not limited thereto. For example, the selection number may be a number other than 3. The selection method may be a method of selecting a value satisfying a predetermined threshold.

At step S3070, the display control unit 114 controls a content to be displayed based on the inference result that is acquired at step S3030 and the information that is selected at step S3060. That is, the display control unit 114 represents the information that is selected by the selection unit 112 as the evidence for inference, and the information is about findings that express the feature of the region that is contained in the medical image of the case that is the subject of the diagnosis assistance.

Figure 6:
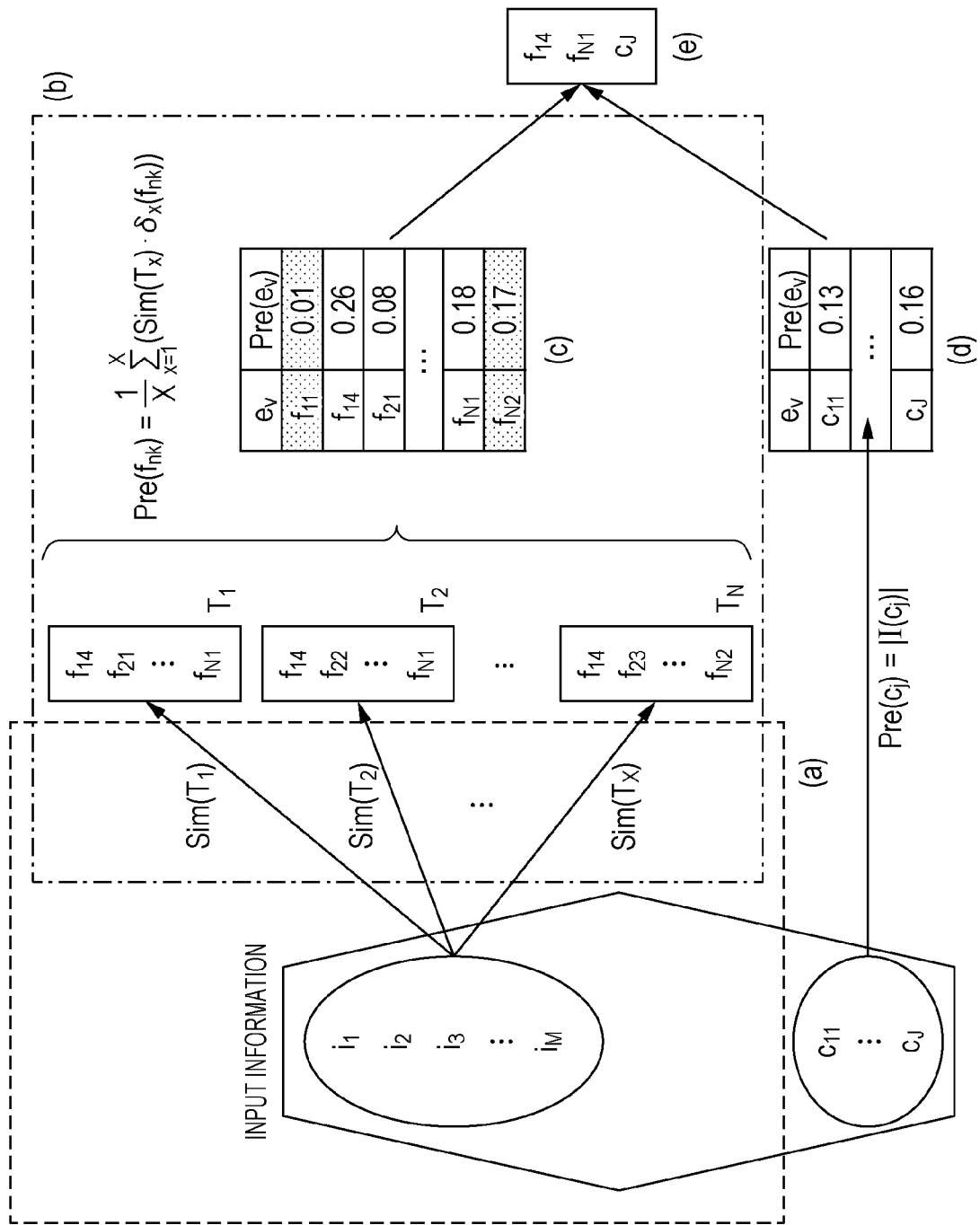
FIG. 6 illustrates an example of information that is acquired by the diagnosis assistance apparatus according to the embodiment of the present invention.

The flow from step S3040 to step S3070 will now be described with reference to FIG. 5 to FIG. 7. For example, the influence degree acquiring unit 108 acquires the influence degree illustrated in FIG. 5 for the elements of the input information that is inputted into the inference unit 106 at step S3040. At step S3050, the presentation degree acquiring unit 110 acquires the degree of similarity with each target case by using the expression 2 regarding image feature amounts $i_1$ to $i_m$ illustrated in (a) of FIG. 6 in the input information. As illustrated in (b) of FIG. 6, the presentation degree acquiring unit 110 acquires the presentation degree by using the degree of similarity with each target case and the image findings that are associated with the target case from the expression 3. Consequently, each image feature amount that is included in the input information is converted into the value of the image findings with the presentation degree. That is, the presentation degree acquiring unit 110 converts M image feature amounts into Y image findings with the presentation degree. Consequently, the presentation degree acquiring unit 110 acquires the image findings with the presentation degree illustrated in (c) of FIG. 6. The presentation degree acquiring unit 110 also acquires the absolute value of the influence degree of the clinical information in the input information as the presentation degree. Consequently, the presentation degree acquiring unit 110 acquires the clinical information with the presentation degree illustrated in (d) of FIG. 6. In this example, all of the cases that are stored in the database, not illustrated, are used. Accordingly, Y is always the same number regardless of the image feature amount of the present case. In the case limited to the top X' case as above or the case limited to the X" case having the degree higher than the threshold, the value of Y may change.

At step S3060, information is selected based on the presentation degree of each element of the image findings and the clinical information. In an example in FIG. 6, the values of the elements in descending order of the magnitude of the presentation degree are $f_{14}$, $f_{N1}$, $f_{N2}$, $c_J$, . . . . However, $f_{N1}$ and $f_{N2}$ have the values of $F_N$, and only $f_{N1}$ the presentation degree of which is higher is taken into account, and $f_{N2}$ is excluded. Accordingly, as illustrated in (e) of FIG. 6, $f_{14}$, $f_{14}$, $F_{N1}$, and $c_J$ are finally selected as the reference information, that is, the information to be represented as the evidence for inference. That is, in the case where findings that express the same feature include findings having different representations in the candidates of the reference information, the selection unit 112 selects information about findings having a high presentation degree as the reference information, that is, the evidence for inference.

Figure 7:
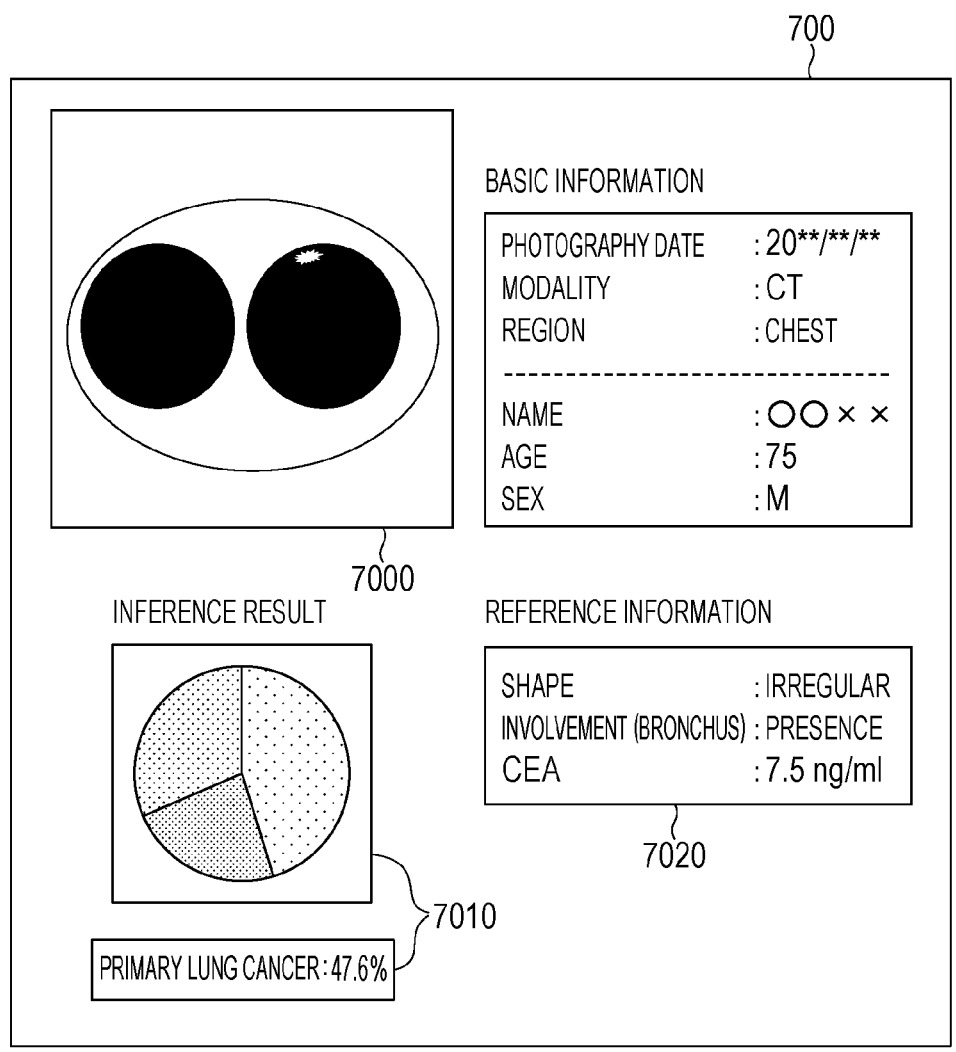
FIG. 7 illustrates an example of a screen that is displayed by the diagnosis assistance apparatus according to the embodiment of the present invention.

FIG. 7 illustrates an example of a screen that is displayed on the monitor 205 by the display control unit 114 at step S3070. A displayed content 700 includes a medical image 7000 that is acquired at step S3000, an inference result 7010 that is acquired at step S3030, and reference information 7020 that is selected at step S3060. The user can use the inference result 7010 and the reference information 7020 that are displayed as assistance information during image diagnosis.

According to the first embodiment, the diagnosis assistance apparatus 100 performs inference based on the input information related to the medical image and acquires the influence degree of each element of the input information on the inference result. The presentation degree is acquired by using the influence degree of each element. In particular, in the case where the input information includes the image feature amount, the image feature amount is converted into the image findings with the presentation degree, and the clinical information and the image findings to be the reference information are represented based on the presentation degree. This enables the doctor corresponding to the user to grasp the information about the evidence for inference in the form of the image findings and the clinical information that are easy to understand by human beings.

(First Modification to First Embodiment)

In an example described according to the first embodiment, at step S3050, the similar case is searched, and the image feature amount is converted into the image findings. It is not limited to this, for example, conversion into the image findings with the presentation degree may be carried out by inferring a likelihood of the value of the image findings from the image feature amount. At this time, only the image feature amount having an influence degree equal to or more than a threshold may be used, and the rest may be a missing value. Only the image feature amounts having top N influence degrees may be used. The presentation degree may be the likelihood of the image findings. The average values, the maximum values, or the minimum values of the influence degrees of the image feature amounts, for example, may be added.

(Second Modification to First Embodiment)

In the example described according to the first embodiment, at step S3050, the similar case is searched, and the image feature amount is converted into the image findings. This is not a limitation. Conversion into the image findings with the presentation degree may be carried out by using a correlation ratio between the image feature amount and the image findings. For example, the presentation degree acquiring unit 110 acquires a correlation ratio $\eta_{mn}$ between the image feature amount $i_m$ and the image findings $F_n$ of a case that is stored in the database and acquires the average of the product of the influence degree of the image feature amount and the correlation ratio. For example, the presentation degree acquiring unit 110 acquires the presentation degree Pre ($F_n$) of the image findings $F_n$ expressed as expression 4.

$$Pre(F_n) = \frac{1}{M}\sum_{m=1}^{M} \{I(i_m) \cdot \eta_{mn}\} \quad \text{(expression 4)}$$

In another example, $F_n$ may be factored, k category values that are 1 if there is $f_{nk}$ and 0 if not for the value of the image findings may be generated to acquire the correlation ratio, and the presentation degree of the value $f_{nk}$ of the image findings may be acquired. The presentation degree of the value $f_{nk}$ of the image findings is expressed as expression 5, where $\eta_{mnk}$ is the correlation ratio between the image feature amount $i_m$ and the image findings $f_{nk}$.

$$Pre(f_{nk}) = \frac{1}{M}\sum_{m=1}^{M} \{I(i_m) \cdot \eta_{mnk}\} \quad \text{(expression 5)}$$

That is, when the presentation degree is acquired, the correlation ratio that is defined in advance may be used as statistics information about representation of the image feature amount by using the image findings.

Second Embodiment

According to a second embodiment, the diagnosis assistance apparatus 100 determines the image findings that are converted from the image feature amount to be the input information for inferring and represents inference and the evidence for inference.

The functional components of the diagnosis assistance apparatus 100 according to the second embodiment is the same as the functional components according to the first embodiment in FIG. 1. However, the function thereof partly differs from that according to the first embodiment. In the following description, only differences from the first embodiment will be described.

The input information generating unit 102 generates the input information based on the information (the medical image, the clinical information, and the supplementary information) that is transmitted from the case information terminal 200 to the diagnosis assistance apparatus 100. According to the second embodiment, the input information generating unit 102 outputs the medical image and the supplementary information to the image feature amount acquiring unit 104. The input information generating unit 102 acquires the image feature amount that is outputted from the image feature amount acquiring unit 104. The input information generating unit 102 performs inference based on the acquired image feature amount, and conversion into the image findings with the likelihood is carried out. The converted image findings and the clinical information are determined to be the input information and outputted to the inference unit 106, the influence degree acquiring unit 108, and the presentation degree acquiring unit 110. The input information generating unit 102 is an example of the findings acquiring means for acquiring the information about the findings based on the image feature amount. The input information generating unit 102 may acquire the information about the image findings from an external server (not illustrated) that provides a function of inferring the image findings based on the image feature amount or may cause a module (for example, the inference unit 106 or a second inference unit) that differs from the input information generating unit 102 to perform the inference.

The inference unit 106 performs inference based on the input information that is generated by the input information generating unit 102. The input information includes the image findings that are converted from the image feature amount. That is, the inference unit 106 is an example of the inference means for inferring the diagnosis that is derived from the medical image, based on the image feature amount.

The presentation degree acquiring unit 110 acquires the presentation degree of each candidate of the reference information, based on the image findings with the likelihood that are generated by the input information generating unit 102 and the influence degree that is acquired by the influence degree acquiring unit 108. The presentation degree acquiring unit 110 outputs the acquired presentation degree of each candidate of the reference information to the selection unit 112.

The hardware configuration of the diagnosis assistance apparatus 100 is the same as that according to the first embodiment in FIG. 2. That is, the function (software) of the diagnosis assistance apparatus 100 and processes illustrated in the flowchart in FIG. 3 by way of example are performed by running the programs that are stored in the main memory 202 and the magnetic disk 203 by the CPU 201. The diagnosis assistance apparatus 100 may include multiple processors. For example, the diagnosis assistance apparatus 100 may include the respective FPGAs in which the functions of the input information generating unit 102 that infers the image findings based on the image feature amount and the inference unit 106 that infers the diagnosis that is derived from the medical image are programed.

FIG. 3 is the flowchart illustrating an example of processing that is performed by the diagnosis assistance apparatus 100 according to the second embodiment. The above description is referred for processes like to those according to the first embodiment to omit a detailed description thereof. In the following description, differences from the first embodiment will be described.

The processes at step S3000 and step S3010 are the same as those according to the first embodiment.

At step S3020, the input information generating unit 102 converts the clinical information that is acquired at step S3000 and the image feature amount that is acquired at step S3010 into the image findings and generates the input information. That is, the input information generating unit 102 acquires the information about the findings by performing inference regarding the image feature amount that is acquired at step S3010. In an example described according to the second embodiment, the input information generating unit 102 performs the inference based on the image feature amount, and the image findings are converted into the image findings with the likelihood.

For example, in the case to be considered herein, the image findings to be converted from the image feature amount $\{i_1, i_2, \ldots, i_M\}$ correspond to a shape ($F_1$: $f_{11}$, $f_{12}$, $f_{13}$, $f_{14}$). The input information generating unit 102 outputs the likelihood of $f_{11}$, $f_{12}$, $f_{13}$, and $f_{14}$ by using the image feature amount as an input. When the likelihood of $f_{11}$ is referred to as L ($f_{11}$), L ($f_{11}$)+L ($f_{12}$)+L ($f_{13}$)+L ($f_{14}$)=1.0 holds. For inference regarding the image findings, various methods that can output the value of the image findings with the likelihood can be used. According to the second embodiment, a multi-value neural network is used. In the following description, the converted image findings with the likelihood are expressed as $F_1(\ )$. That is, the input information generating unit 102 acquires the information about the findings corresponding to the image feature amount and acquires the likelihood, that is the statistics information, about representation of the image feature amount by using the findings.

The input information generating unit 102 generates a set of the converted image findings and the clinical information as the input information. The image findings that is used as the input information have the likelihood. For example, when the clinical information is expressed as $\{c_{12}, c_{22}, \ldots, c_J\}$, and the converted image findings are expressed as $\{F_1(\ ), F_2(\ ), \ldots\}$, the input information $E_f$ is expressed as $E_f=\{c_{12}, c_{22}, \ldots, c_J, F_1(\ ), F_2(\ ), \ldots\}$.

At step S3030, the inference unit 106 performs inference related to the abnormal shadow on the lungs to be diagnosed, based on the input information that is generated at step S3020. A Bayesian network is used for the inference method as in the first embodiment. That is, the inference unit 106 performs the inference by using the information about the findings that is acquired based on the image feature amount as the input information.

According to the second embodiment, the value of the image findings is expressed by the likelihood. Accordingly, regarding all combinations of the image findings, inference is performed, and the inference result is integrated by using the likelihood. In an example described herein, the image findings are expressed as $F_a\{f_{a1}, f_{a2}\}$, $F_b\{f_{b1}, f_{b2}\}$, and the clinical information is expressed as $\{c_J\}$. The inference unit 106 generates temporary input information ($E_z$) in consideration of all combinations of the elements that are included in the input information. In this case, the inference unit 106 generates four pieces of the temporary input information of $E_1=\{f_{a1}, f_{b1}, c_J\}$, $E_2=\{f_{a1}, f_{b2}, c_J\}$, $E_3=\{f_{a2}, f_{b1}, c_J\}$, $E_4=\{f_{a2}, f_{b2}, c_J\}$. The inference unit 106 acquires P ($d_s|E_z$) by using the pieces of the temporary input information. The inference unit 106 adds the likelihood of the image findings to P ($d_s|E_z$) and finally acquires the inference result by adding the result. In the above example, the inference unit 106 finally acquires the inference result P ($d_s|E_f$) expressed as L ($f_{a1}$)×L ($f_{b1}$)×P ($d_s|E_1$)+ . . . +L ($f_{a2}$)×L ($f_{b2}$)×P ($d_s|E_4$). In the above example, the inference result can be expressed as expression 6.

$$P(d_s|E_f) = \Sigma_{z=1}^{Z} \{\Pi_{f_{nk} \in E_z} L(f_{nk})\} P(d_s|E_z) \rfloor \quad \text{(expression 6)}$$

That is, the inference unit 106 generates the pieces of the temporary input information from at least a part of the information about the findings that is included in the inputted information and infers the diagnosis based on the result of inference performed based on the pieces of the temporary input information and the likelihood, that is, the statistics information. The inference unit 106 may ignore the value of the image findings the likelihood of which is equal to or less than a threshold to decrease the number of acquisitions.

The process at step S3040 is the same as that according to the first embodiment.

At step S3050, the presentation degree acquiring unit 110 acquires the presentation degree by using the likelihood of the image findings that is acquired at step S3020 and the influence degree that is acquired at step S3040. The presentation degree acquiring unit 110 acquires the absolute value of the influence degree of each element of the clinical information as the presentation degree. The presentation degree acquiring unit 110 also acquires the product of the absolute value of the influence degree and the likelihood of the image findings converted by the input information generating unit 102 as the presentation degree. That is, the presentation degree acquiring unit 110 acquires the presentation degree L ($f_{nk}$)×I ($f_{nk}$) based on the influence degree and the likelihood that is an example of the statistics information regarding the image findings.

The processes at step S3060 and step S3070 are the same as those according to the first embodiment. That is, the selection unit 112 selects the information to be represented as the evidence for inference based on the presentation degree that has a value based on the influence degree of the information about the findings included in the input information on the inference and the statistics information about representation of a region that the image feature amount expresses by using the information about the findings. The display control unit 114 represents the information that is selected by the selection unit 112 as the evidence for inference.

According to the second embodiment, the diagnosis assistance apparatus 100 converts the result of image processing on the medical image into the image findings and determines the converted image findings and the clinical information to be the input information. The presentation degree of each element of the input information is acquired, and the image findings and the clinical information to be the reference information are represented based on the presentation degree. This enables the doctor corresponding to the user to check the reference information in the form of the image findings and the clinical information that are easy to understand by human beings, and the doctor's diagnosis can be supported.

(First Modification to Second Embodiment)

In the described example, at step S3020, the input information generating unit 102 acquires the image findings with the likelihood by inference based on the image feature amount. This is not a limitation. As in, for example, the first embodiment, the similar case may be searched to acquire the information about the findings, or the correlation ratio may be used to acquire the information about the findings.

In the case where the similar case is searched to acquire the information about the findings, for example, the Mahalanobis distance may be used to acquire the degree of similarity Sim ($T_x$), and the likelihood of the findings may be expressed as the expression 3 to acquire the presentation degree.

In the case where the correlation ratio is used to acquire the information about the findings, for example, the likelihood can be acquired by using expression 7.

$$L(f_{nk}) = \frac{1}{M}\sum_{m=1}^{M} \eta_{mnk} \quad \text{(expression 7)}$$

(Second Modification to Second Embodiment)

At step S3030, the temporary input information is generated regarding all combinations of the image findings, and the inference result by using the temporary input information is finally integrated into the inference result. However, there is no need for performance regarding all combinations of the image findings. For example, among the image findings, only the value of the image findings having the highest likelihood may be used for inference.

Third Embodiment

In an example described according to a third embodiment, the input information into the inference unit 106 includes the information about the findings that is acquired based on the image feature amount and information about findings that the doctor, for example, inputs as the supplementary information.

The functional components of the diagnosis assistance apparatus 100 according to the third embodiment are the same as those according to the first embodiment in FIG. 1. The hardware configuration of the diagnosis assistance apparatus 100 is the same as that according to the first embodiment in FIG. 2. That is, the function (software) of the diagnosis assistance apparatus 100 according to the third embodiment and the processes illustrated in the flowchart in FIG. 3 by way of example are performed by running the programs that are stored in the main memory 202 and the magnetic disk 203 by the CPU 201.

FIG. 3 is the flowchart illustrating an example of processing that is performed by the diagnosis assistance apparatus 100 according to the third embodiment. The above description is referred for processes like to those according to the first embodiment to omit a detailed description thereof. In the following description, differences from the first embodiment will be described.

The processes at step S3000 and step S3010 are the same as those according to the first embodiment.

At step S3020, the input information generating unit 102 generates the input information based on the clinical information that is acquired at step S3000, image findings that are included in the supplementary information, and the image feature amount that is acquired at step S3010. For example, in the case to be considered herein, the clinical information that is acquired at step S3000 is expressed as $\{c_{12}, c_{22}, \ldots, c_J\}$, the image findings that are included in the supplementary information are expressed as $\{f_{11}, f_{31}\}$, and the image feature amount that is acquired at step S3010 is expressed as $\{i_1, i_2, \ldots, i_M\}$. In this case, the input information $E_f$ is expressed as $E_f = \{c_{12}, c_{22}, \ldots, c_J, f_{11}, f_{31}, i_1, i_2, \ldots, i_M\}$.

The processes at step S3030 and step S3040 are the same as those according to the first embodiment.

At step S3050, the presentation degree acquiring unit 110 calculates the presentation degree of each candidate of the reference information by using the influence degree that is calculated at step S3040. The presentation degree acquiring unit 110 acquires the absolute value of the influence degree of each element of the clinical information and the image findings as the presentation degree. The presentation degree acquiring unit 110 converts the image feature amount into the image findings with the presentation degree.

According to the third embodiment, the similar case is searched to acquire the image findings based on the image feature amount as in the first embodiment. It is thought that the image findings that are acquired by searching the similar case duplicate the image findings that are inputted by the doctor. In the case where the image findings are thus duplicated, for example, the presentation degree acquiring unit 110 determines that the image findings that are acquired by searching the similar case are not included in the candidates of the reference information. For example, in the case to be considered herein, the image findings that are included in the input information are referred to as $f_{11}$, and the image findings with the presentation degree are illustrated in (c) of FIG. 6. In this case, the doctor inputs $f_{11}$ that is the value of $F_1$. Accordingly, among the image findings with the presentation degree, $f_{11}$, and $f_{14}$ that are the values of $F_1$ are not included in the candidates of the reference information, and, for example, the presentation degree is set to zero. Accordingly, regarding $F_1$, only $f_{11}$ is included in the candidates of the reference information. The presentation degree of $f_{11}$ that is included in the supplementary information is the absolute value of the influence degree.

The processes at step S3060 and step S3070 are the same as those according to the first embodiment.

According to the third embodiment, in the case where the image findings are included in the supplementary information, the diagnosis assistance apparatus 100 determines the image feature amount, the image findings, and the clinical information to be the input information. Inference is performed based on the input information, and the influence degree of each element of the input information on the inference result is acquired. The presentation degree is also acquired by using the influence degree of each element. However, in the case where the image findings that are converted from the image feature amount duplicate the image findings that are included in the input information, the latter image findings have priority. This enables the inference to be performed with the image findings that are inputted by the doctor corresponding to the user and enables the reference information to be represented in the form of the image findings and the clinical information that are easy to understand by human beings. Furthermore, the user can check the evidence for inference also in consideration of user's own thoughts.

Fourth Embodiment

A diagnosis assistance apparatus according to a fourth embodiment generates the input information into the inference unit by using a derivation unit that is constructed by machine learning. The construction of an inferencer used when the diagnosis assistance apparatus infers the diagnosis needs a large amount of data sets including the required information. From a data set including information about diagnosis and a medical image, an inferencer that infers the diagnosis by using a new medical image as an input can be constructed. From a data set including a medical image and information about image findings that express a feature that the doctor reads from the medical image by wording, an inferencer that infers the image findings by using a new medical image as an input can be constructed. However, there is a possibility that a large amount of data sets including the medical image and the information about the image findings cannot be acquired. It is an object of the fourth embodiment to construct an inferencer having high precision even if only a small amount of information needed for a data set that can be used to construct the inferencer is acquired, and to provide a diagnosis assistance apparatus by using the inferencer.

Figure 8:
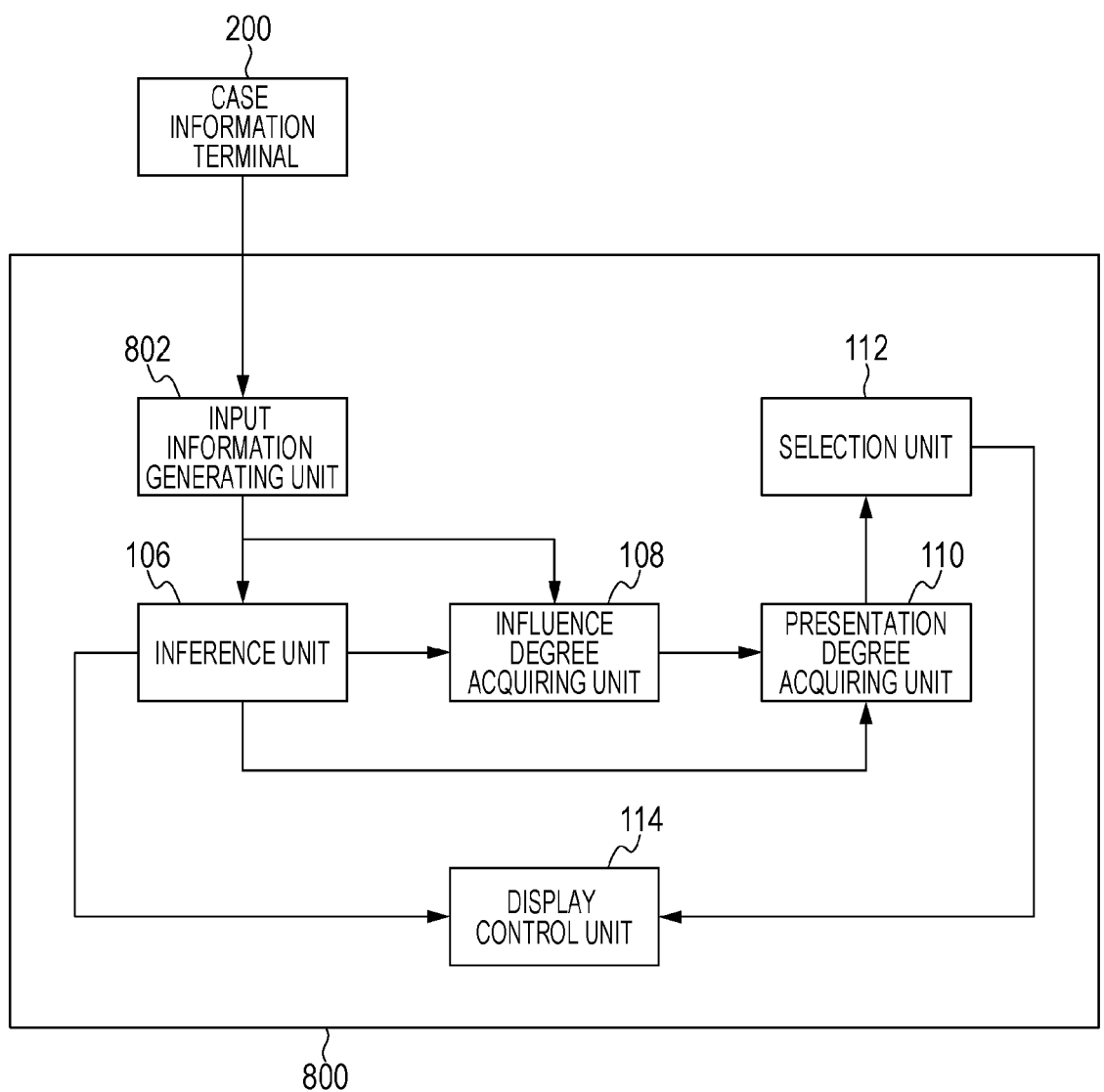
FIG. 8 illustrates an example of the functional components of a diagnosis assistance apparatus according to a fourth embodiment of the present invention.

FIG. 8 illustrates an example of the functional components of a diagnosis assistance apparatus 800 according to the fourth embodiment. Functional components like to those of the diagnosis assistance apparatus 100 according to the second embodiment are designated by like reference characters, and the above description is referred to omit a detailed description thereof here. According to the fourth embodiment, an input information generating unit 802 has the function of the image feature amount acquiring unit 104 in addition to the function of the input information generating unit 102 according to the second embodiment. That is, the input information generating unit 802 according to the fourth embodiment derives the image findings based on the information (the medical image, the clinical information, and the supplementary information) that is acquired from the case information terminal 200.

Figure 9:
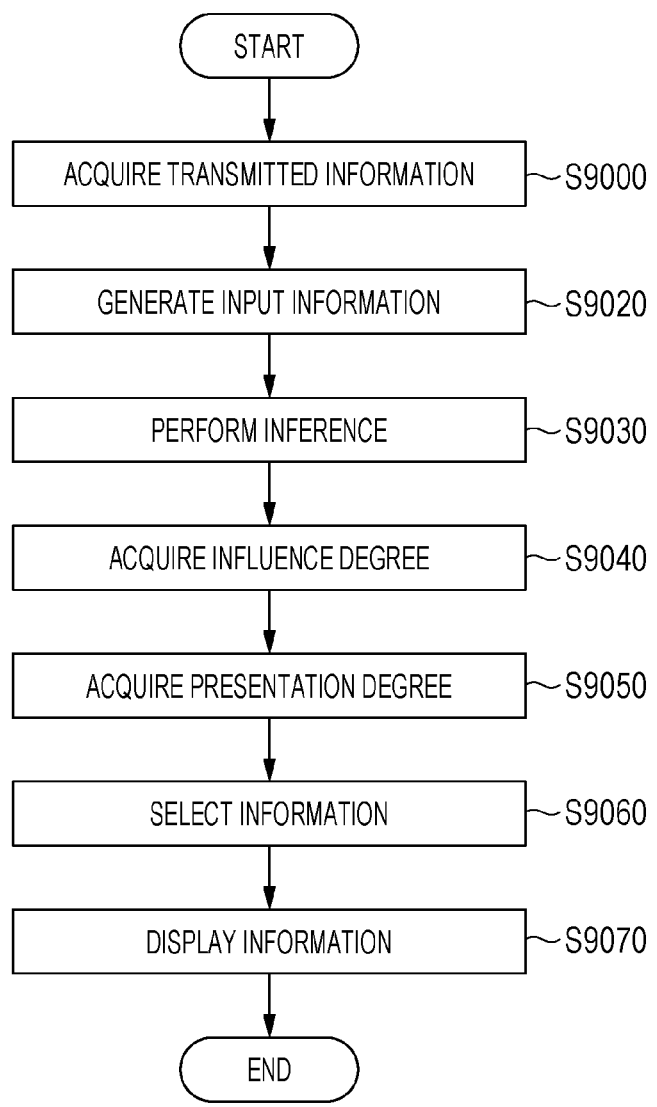
FIG. 9 is a flowchart illustrating an example of processing that is performed by the diagnosis assistance apparatus according to the fourth embodiment of the present invention.

FIG. 9 is a flowchart illustrating an example of processing that is performed by the diagnosis assistance apparatus 800 according to the fourth embodiment. The above description is referred for processes like to those according to the second embodiment to omit a detailed description thereof. In the following description, differences from the second embodiment will be described.

The process at step S9000 is the same as that at step S3000 according to the second embodiment.

At step S9020, the input information generating unit 802 derives the image findings with the likelihood based on the information that is acquired at step S9000. The input information generating unit 802 generates a set of the derived image findings and the clinical information as the input information.

The process of deriving the image findings with the likelihood by the input information generating unit 802 is performed by using derivation units (classifiers) that classify the medical image into any one of the values of finding items. The number of the derivation units that are created is equal to the number of the finding items. That is, a derivation unit that classifies the shape ($F_1$: $f_{11}$, $f_{12}$, $f_{13}$, $f_{14}$) differs from a derivation unit that classifies the cut ($F_2$: $f_{21}$, $f_{22}$, $f_{23}$). The derivation units are constructed by a CNN (Convolutional Neural Network) by using a data group in which a correct label of classification for every finding item is added to the medical image. The CNN is an example of machine learning. The input information generating unit 802 can also acquire the likelihood of the classification by processing the output of a classification model by using a softmax function.

A medical image that is preprocessed may be inputted into the derivation units. For example, a partial image that is obtained based on the position of the abnormal shadow by cutting a ROI (Region of Interest) or a VOI (Volume of Interest) from the medical image may be inputted. An image that is obtained by performing a mask process on a specific region or an image on which image processing such as contrast enhancement is performed may be inputted.

The processes at steps S9030 to S9070 are the same as those at steps S3030 to S3070 according to the second embodiment.

The inference unit 106 according to the fourth embodiment thus infers the diagnosis by using the derivation units (the input information generating unit 802) that output the information about the image findings based on the medical image and outputs the information about the image findings to be the evidence for inference. The diagnosis assistance apparatus according to the fourth embodiment represents the inferred diagnosis and the information about the image findings to be the evidence for inference to the user by using the derivation units that output the information about the image findings based on the medical image.

According to the fourth embodiment, processing for deriving the findings with the likelihood is constructed by the CNN. This enables the findings to be derived with precision even if there is an unknown image feature amount that affects the findings. As in the second embodiment, the doctor corresponding to the user can grasp the information about the evidence for inference of the diagnosis in the form of the image findings and the clinical information that are easy to understand by human beings.

(First Modification to Fourth Embodiment)

Figure 10:
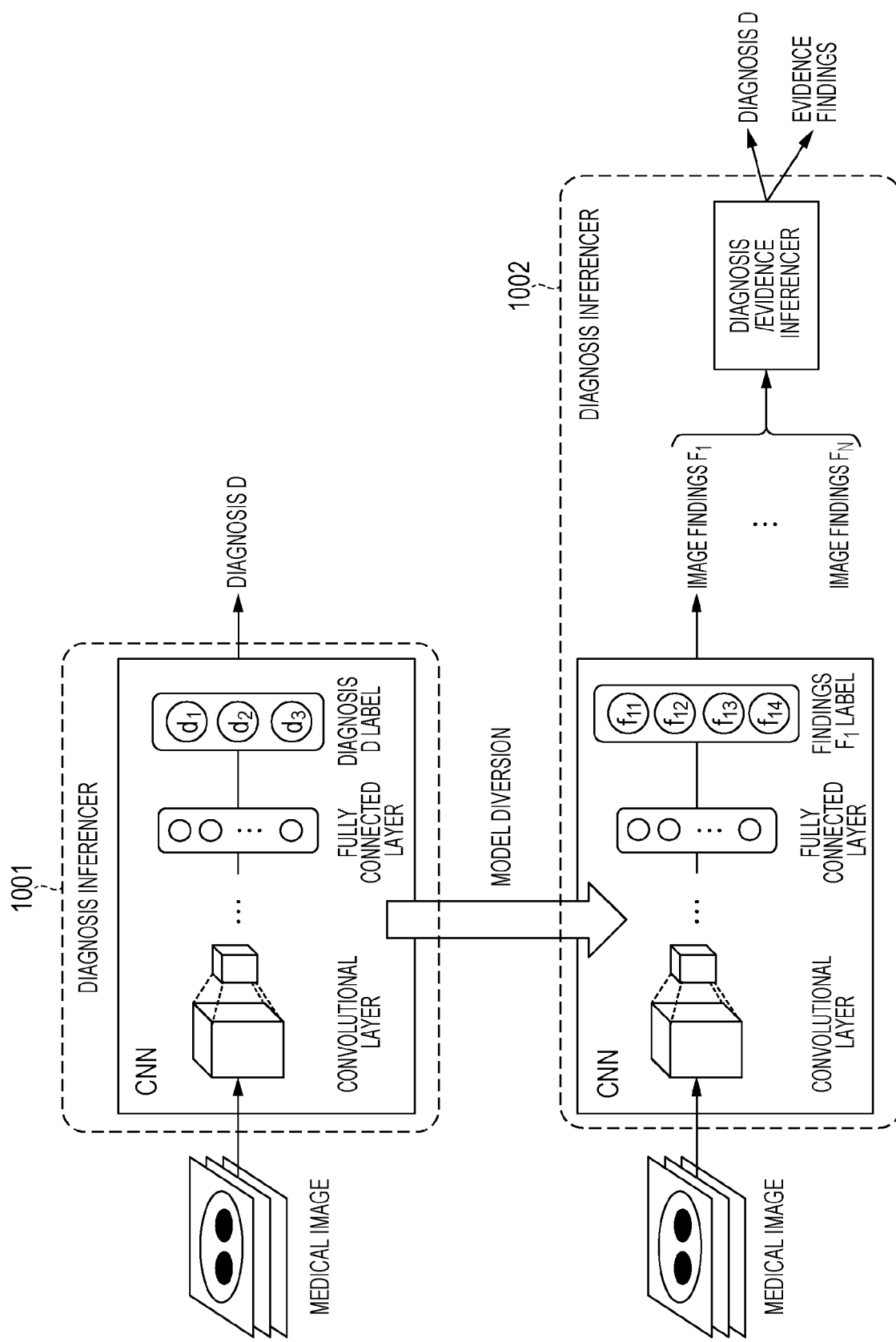
FIG. 10 illustrates an example of a method of generating a derivation unit by using the diagnosis assistance apparatus according to the fourth embodiment of the present invention.

The derivation units that classify the medical image into any one of the values of the finding items may be created by diverting a model of a derivation unit created for another purpose. For example, as illustrated in FIG. 10, a diagnosis inferencer 1001 that is a derivation unit that classifies the medical image into diagnosis is constructed by the CNN, and the model thereof is diverted to construct a diagnosis inferencer 1002 that is a derivation unit that classifies the medical image into any one of the values of the finding items. The model is diverted by using a method disclosed in, for example, Japanese Patent Application Laid-Open No. 2017-84320. That is, a diverted model having the same structure and parameters as those of the original model except for a final layer is prepared, and the parameters of the model are updated by relearning with a data set for the purpose. The model may be diverted in another manner, for example, by using only the same convolutional layer as that of the original model.

The original model is not limited to a derivation unit for diagnosis. For example, a model that is created by a known learning method without a teacher such as auto encoder may be diverted.

In this case, as illustrated in FIG. 10, there are two diagnosis inferencers that infer the diagnosis based on the medical image. One of the diagnosis inferencers is the diagnosis inferencer 1001 that infers the diagnosis directly from the medical image. The other is the diagnosis inferencer 1002 that infers the diagnosis via the findings from the medical image. The diagnosis inferencer 1002 can also acquire the information to be the evidence for inference by using the presentation degree acquiring unit 110 and the selection unit 112.

That is, the diagnosis inferencer 1002 is acquired by using data set groups collected in advance as follows. The data set groups include at least the information about the diagnosis. In a first process, a first inferencer that infers the diagnosis from the medical image is acquired by machine learning. The diagnosis inferencer 1001 is an example of the first inferencer. In a second process, a second inferencer that has a structure a part of which is common to a part of the structure of the first inferencer and that infers the image findings that express an image feature from the medical image is acquired by machine learning. An inferencer that is constructed by the CNN included in the diagnosis inferencers illustrated in FIG. 10 is an example of the second inferencer. In a third process, a third inferencer that infers the diagnosis from the image findings and that outputs the information about the image findings to be the evidence for inference is acquired. A diagnosis/evidence inferencer that is included in the diagnosis inferencer 1002 illustrated in FIG. 10 is an example of the third inferencer. In a fourth process, a fourth inferencer that infers the diagnosis from the medical image based on the second inferencer and the third inferencer is acquired. The diagnosis inferencer 1002 is an example of the fourth inferencer. The third process relevant to acquisition of the diagnosis inferencer 1002 may be performed before the first process and the second process or may be performed in parallel.

The diagnosis assistance apparatus 800 according to the fourth embodiment may use the diagnosis inferencer 1001 or the diagnosis inferencer 1002 instead of the input information generating unit 802 and the inference unit 106. Alternatively, both of the diagnosis inferencer 1001 and the diagnosis inferencer 1002 are may be used.

When the inferred diagnosis is represented to the user, information about the precision of the used diagnosis inferencer may also be represented. The precision of the diagnosis inferencer is acquired in a manner in which a data set group that is not used for acquiring (during learning) the diagnosis inferencers among the data set groups collected in advance is used as an evaluation data set group, and a proportion of the number of times the correct label and the inference result coincide with each other is used. The inference unit 106 may include an evaluation unit (not illustrated) that evaluates the precision of the used diagnosis inference, or the diagnosis assistance apparatus 800 may include the evaluation unit (not illustrated). The evaluation unit (not illustrated) is an example of an evaluation means.

The evaluation unit (not illustrated) may calculate the precision of diagnosis inference for every image classification. That is, the evaluation unit (not illustrated) may evaluate the precision for every category that is classified by an image feature. An example of the category is a structure of a subject to be diagnosed that is drawn in the medical image. The evaluation unit (not illustrated) may calculate the precision, for example, regarding an image containing the chest wall and an image containing no chest wall. When a new image containing the chest wall is inputted as the subject of inference, the inference unit 106 may use a diagnosis inferencer having high precision for the category of the image containing the chest wall. This enables the inference unit 106 to select the diagnosis inferencer suitable for the inputted image.

The diagnosis that is represented to the user may be selected from the inference result of the diagnosis inferencer having high precision. The results of the two diagnosis inferencers may be represented at the same time.

The diagnosis inferencer to be used may be selected by the presence of a supplementary function, for example, whether the evidence for inference is provided. This enables the inferencer suitable for the circumstances of the user to be selected, for example, if the user explicitly inputs the findings, the diagnosis inferencer 1002 that can provide the evidence for inference is used, and if the user looks at an image, the diagnosis inferencer having high precision is used. That is, the inference unit may select the inferencer based on an operation input of the user.

In the case where the diagnosis inferencer 1002 infers the diagnosis and the evidence for inference at the same time as the diagnosis inferencer 1001 infers the diagnosis, and the inference results of the diagnosis inferencers are the same as each other, the evidence for inference and the inference result of the diagnosis inferencer 1002 may be represented to the user. In the case where the inference results differ from each other, the inference result of the inferencer having higher precision may be represented to the user. This enables the diagnosis inferencer suitable for the inputted image to be selected.

According to the present modification, a model that learns in advance such that a feature of the medical image is acquired is diverted, and this enables the findings to be derived by the CNN with precision even if there are a small number of the data groups in which the correct label of the findings is added to the medical image.

(Second Modification to Fourth Embodiment) According to the first modification to the fourth embodiment, the output of an intermediate layer of the original model may be extracted as an image feature to be used as an image feature amount extracting unit. The image feature amount extracting unit is used as a part of the input information generating unit 802 according to the fourth embodiment. That is, the input information generating unit 802 derives the findings based on the image feature that is extracted by the image feature amount extracting unit by using a method such as a support vector machine or random forests.

According to the present modification, a model that learns in advance such that a feature of the medical image is acquired is diverted, and this enables the findings to be derived with precision even if there are a small number of the data groups in which the correct label of the findings is added to the medical image.

According to the above-mentioned embodiments and modifications of the present invention, information to be an evidence for inference can be represented by using information about findings that a doctor can readily grasp, and the doctor can readily decide whether the result of the inference is useful for diagnosis.

[Modification]

An information-processing apparatus according to the embodiments described above may be a single apparatus, or a plurality of apparatuses may be combined so as to be able to communicate with each other to perform the above processes. These are included in the embodiments of the present invention. The above processes may be performed by a common server apparatus or a server group. It is not necessary for a plurality of apparatuses that serve as the information-processing apparatus and an information-processing system to be installed in the same facility or the same country provided that the apparatuses can communicate at a predetermined communication rate.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

An appropriate combination of the above embodiments is also included in the embodiments of the present invention.

The present invention is not limited to the above embodiments. Various modifications and alterations can be made without departing form the spirit and scope of the present invention. Accordingly, the following claims are attached to publish the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing method comprising:
   acquiring a first inferencer configured to infer a first diagnosis from a first subject medical image by machine learning using a first data set of medical images; and
   acquiring a second inferencer configured to have a structure a part of which is common to a part of a structure of the first inferencer and infer a set of image findings that expresses an image feature from a second subject medical image by machine learning using a second data set of medical images.

2. An information processing system comprising:
   one or more processors; and
   a memory storing instructions that, when executed by the one or more processors, cause the information processing system to:
   acquire a first inferencer configured to infer a first diagnosis from a first subject medical image by machine learning using a first data set of medical images; and
   acquire a second inferencer configured to have a structure a part of which is common to a part of a structure of the first inferencer and infer a set of image findings that expresses an image feature from a second subject medical image by machine learning using a second data set of medical images.

3. A diagnosis assistance apparatus comprising at least one of (a) one or more processors and (b) circuitry, (a) and (b) each configured to function as:
   a plurality of inferencers inferring from a medical image;
   an inference means inferring by using at least one of the plurality of inferencers and by using a medical image as an input into the at least one of the plurality of inferencers; and
   a representation means representing an inference result by the inference means,
   wherein a second inferencer that is included in the plurality of inferencers infers an image finding that expresses an image feature by using a medical image as an input, and the second inferencer has a structure a part of which is common to a part of a structure of a first inferencer inferring diagnosis.

4. The diagnosis assistance apparatus according to claim 3, wherein the first inferencer is included in the plurality of inferencers.

5. The diagnosis assistance apparatus according to claim 3, wherein the first inferencer and the second inferencer have the same structure in a predetermined layer.

6. The diagnosis assistance apparatus according to claim 5, wherein the first inferencer and the second inferencer have the same parameter of the predetermined layer.

7. The diagnosis assistance apparatus according to claim 5, wherein the first inferencer and the second inferencer have the same structure in at least a part of at least one of an input layer and an intermediate layer.

8. The diagnosis assistance apparatus according to claim 6, wherein the first inferencer and the second inferencer have the same structure in and the same parameter of a convolutional layer that is an intermediate layer.

9. The diagnosis assistance apparatus according to claim 3, wherein the second inferencer is an inferencer having a parameter updated from a parameter in a predetermined layer of the first inferencer by further learning using a data set.

10. A diagnosis assistance system comprising at least one of (a) one or more processors and (b) circuitry, (a) and (b) each configured to function as:
    a plurality of inferencers inferring from a medical image;
    an inference means inferring by using at least one of the plurality of inferencers and by using a medical image as an input into the at least one of the plurality of inferencers; and
    a representation means representing an inferred result by the inference means,
    wherein a second inferencer that is included in the plurality of inferencers infers an image finding that expresses an image feature by using a medical image as an input, and the second inferencer has a structure a part of which is common to a part of a structure of a first inferencer inferring diagnosis.

11. A diagnosis assistance apparatus comprising at least one of (a) one or more processors and (b) circuitry, (a) and (b) each configured to function as:
    a plurality of inferencers inferring from a medical image;
    an inference means inferring by using at least one of the plurality of inferencers and by using a medical image as an input into the at least one of the plurality of inferencers; and
    a representation means representing an inference result by the inference means,
    wherein a first inferencer that is included in the plurality of inferencers performs a first inference on the medical image as an input,
    a second inferencer that is included in the plurality of inferencers performs a second inference on the medical image as an input, and
    the first inferencer and the second inferencer have a structure a part of which is common to each other.

12. The diagnosis assistance apparatus according to claim 11, wherein the first interference by the first inferencer is an inference different from the second inference by the second inferencer.

* * * * *